United States Patent [19]

Jung et al.

[11] Patent Number: 5,352,236
[45] Date of Patent: Oct. 4, 1994

[54] BALLOON PROTECTOR

[75] Inventors: Eugene Jung, San Diego; Kazuo Sasamine, Lemon Grove, both of Calif.

[73] Assignee: Medtronic, Inc., Minneapolis, Minn.

[21] Appl. No.: 954,780

[22] Filed: Sep. 29, 1992

[51] Int. Cl.⁵ ............................................. A61M 29/00
[52] U.S. Cl. ............................ 606/194; 604/96; 604/103
[58] Field of Search ............... 604/96, 103, 263, 163, 604/171; 606/192, 194, 195; 206/363, 364, 446, 497, 805; 24/16 PB, 300; 403/290

[56] References Cited

U.S. PATENT DOCUMENTS

| | | | |
|---|---|---|---|
| 3,136,417 | 6/1964 | Clinch | 128/844 |
| 4,185,375 | 1/1980 | Brown | 206/446 |
| 4,327,735 | 5/1982 | Hampson . | |
| 4,444,186 | 4/1984 | Wolvek et al. . | |
| 4,573,981 | 3/1986 | McFarlane . | |
| 4,646,722 | 3/1987 | Silverstein et al. | 128/4 |
| 4,681,092 | 7/1987 | Cho et al. . | |
| 4,702,252 | 10/1987 | Brooks et al. | 606/195 |
| 4,710,181 | 12/1987 | Fuqua . | |
| 4,738,666 | 10/1991 | Fuqua . | |
| 5,015,231 | 5/1991 | Keith et al. | 604/96 |
| 5,053,007 | 10/1991 | Euteneuer . | |
| 5,066,298 | 11/1991 | Hess . | |
| 5,116,318 | 5/1992 | Hillstead | 606/194 |
| 5,137,512 | 8/1992 | Burns et al. . | |
| 5,211,654 | 5/1993 | Kaltenbach | 606/194 |

*Primary Examiner*—John D. Yasko
*Assistant Examiner*—Anthony Gutowski
*Attorney, Agent, or Firm*—Dianne M. F. Plunkett; Harold R. Patton

[57] ABSTRACT

An elastomeric compression unit forming a balloon protector for a catheter and a catheter system having the balloon protector are disclosed. The balloon protector is formed of an elastomeric tube, preferably silicone, lined with lubricious material. The lubricious lining may be a coating such as silicone or may be a Teflon TM tube. The Teflon TM tube is split longitudinally, so that the compressive forces of the protector are transmitted through it to the balloon. In the preferred embodiment, the split is made tangential to the inner surface of the Teflon TM tube. In the catheter system, the inner lumen is preferably non-compressible, or a stylet is inserted within it to preclude its compression.

10 Claims, 3 Drawing Sheets

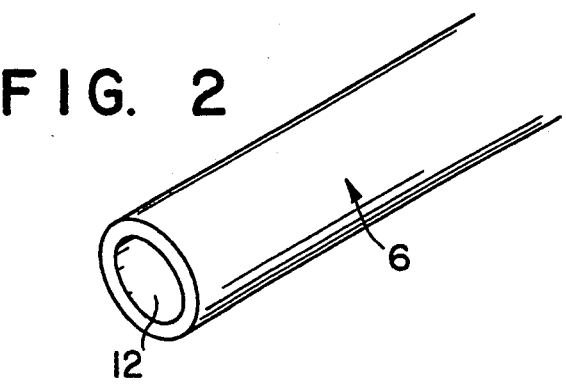
FIG. 2
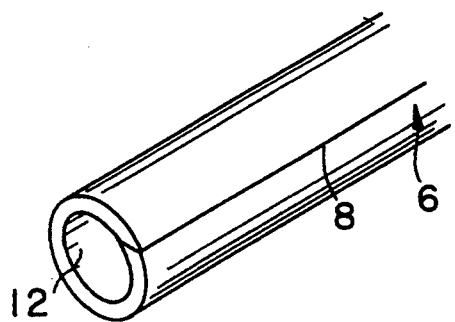
FIG. 3
FIG. 4
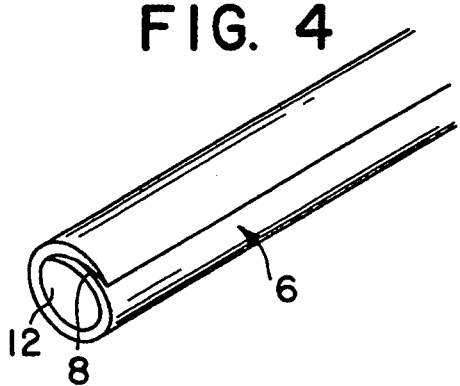
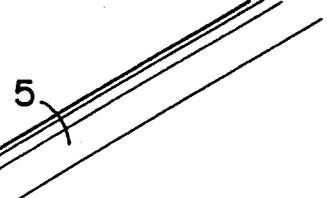
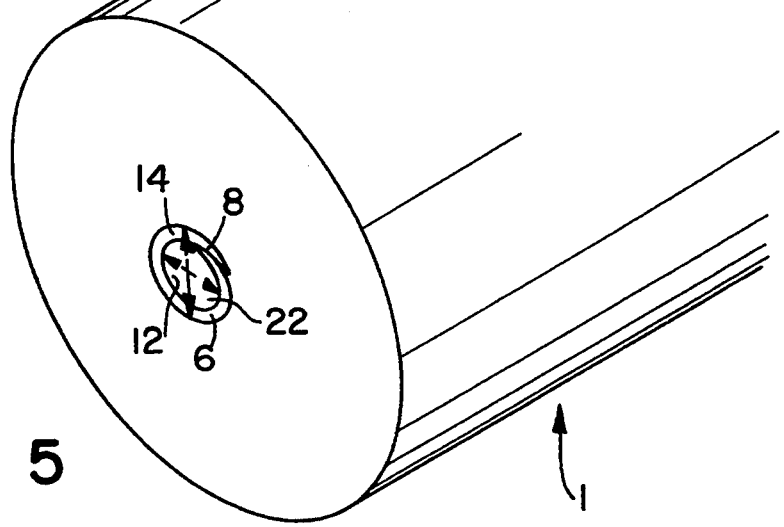
FIG. 5

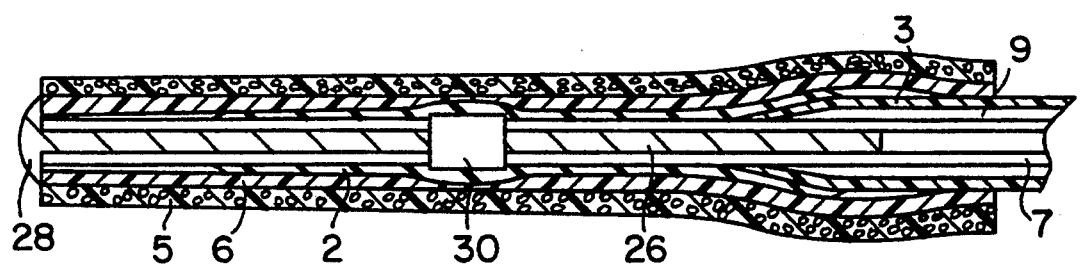
F I G. 6

BALLOON PROTECTOR

BACKGROUND OF THE INVENTION

1. Field of the Invention

This invention relates to protectors for the balloon of a balloon catheter.

2. Description of the Prior Art

Angioplasty has gained wide acceptance in recent years as an efficient and effective method for opening stenoses in the coronary arteries and in other parts of the vascular system. The most widely used form of angioplasty catheter includes an inflatable balloon at its distal end for dilation of the stenosis.

Using fluoroscopy, the physician guides the catheter through the vascular system until the balloon is positioned across the stenosis. The balloon is then inflated by supplying a fluid under pressure through an inflation lumen to the balloon. The inflation of the balloon clears the pathway through the artery.

One important characteristic of a dilatation balloon catheter used for angioplasty is its "profile", which is determined by the outer diameter of the distal end portion of the balloon, because a smaller diameter balloon (and catheter) can be more easily maneuvered through the coronary arteries and into the stenoses. Accordingly, considerable effort has been spent in developing low profile dilatation balloon catheters by minimizing the dimensions of the core or inner tube which extends through the balloon to its distal end, and by reducing wall thicknesses, to the extent possible, of the balloon itself.

Another important consideration is the outer diameter of the balloon in its deflated condition. In order to reduce the outer diameter of the balloon in its deflated condition, it is common to fold and/or wrap the flaps of the deflated balloon. When inflation fluid is applied to the deflated balloon, it causes the balloon flaps to unwrap so that the balloon can inflate to its full inflated state.

It has also been common to use a balloon protector in conjunction with a balloon dilatation catheter. The balloon protector wraps the balloon tightly in its deflated condition to minimize the outer diameter of the balloon in its deflated state. It also protects the balloon and the distal tip of the catheter from possible damage during shipping.

Some current balloon protectors are tubular units made of Teflon TM, the inner diameter varying along the length of the tube so as to provide adequate compression at both the proximal and distal cones, the marker band area, and remaining areas of the balloon. These Teflon TM balloon protectors may be made by heat shrinking a Teflon TM tube down around a mandrel, resulting in a protector having some variability in size. A problem with such protectors is that in combination with the inherent variability in balloon size in any group of catheters, the variance in the balloon protectors may be large enough that all the balloon protectors will not fit any given catheter; the protector must instead be individually selected from the group to fit the catheter.

Another difficulty with current balloon protectors is that a protector which may originally hold the balloon tightly wrapped may become needlessly loose during final processing. The protector is typically placed around the balloon after the balloon is wrapped. The balloon is then heat set in its wrapped form and finally sterilized, all while the balloon protector is in place. The balloon shrinks during both processes, so that the protector may not hold the balloon wrap as tightly as might be desired, once the processes are complete.

In U.S. Pat. No. 5,053,007 to Euteneuer, a several-piece balloon protector is disclosed in which a compressible sleeve surrounding the balloon is compressed by two threaded, interlocking outer sleeves. Although the sleeve is disclosed to be of an elastic material, its inner diameter is slightly greater than the outer diameter of the balloon, and the large outer sleeves mechanically compress it.

In Hess, U.S. Pat. No. 5,066,298 a strip of non-elastic Teflon TM tape is wrapped helically around the balloon to compress it. The wrapping process, however, requires special machinery or time on the part of an operator to successfully wrap it.

Burns, et al., U.S. Pat. No. 5,137,512 discloses a multisegment balloon protector composed of two or more Teflon TM tubes, usually axially aligned and of different diameters, the advantage being that less force is required to apply the protectors, resulting in less damage to the fragile balloons.

Fuqua, in U.S. Pat. Nos. 4,738,666 and 4,710,181, discloses a longitudinally-folded catheter and a sheath which surrounds the catheter to hold it in a folded position. The catheter and sheath are inserted into the body, and the sheath removed so that the catheter unfolds and resumes its original, manufactured state. The sheath may be perforated to aid in removal. There is no indication that the sheath is smaller than, or forms an interference fit with, the catheter.

In Fuqua, the desired sheath is very thin (about 0.008 in.) and the sheath material has a high resilience and resistance to stretch measured by a "doxemeter rating of at least about 65%." Simply put, it appears that the desired sheath material is not elastic; rather it is largely inelastic, holding the catheter, which is compressible, in its folded shape. The intention is to compress the catheter, but not to permanently alter its configuration, since the catheter is intended to resume its original shape once the sheath is removed.

Cho, et al., U.S. Pat. No. 4,681,092, discloses a several-part wrapping apparatus for wrapping an intra-aortic balloon catheter. The device has channels to aid in wrapping the balloon and contains a shoe to bias the balloon in wrapped shape.

Hampson, U.S. Pat. No. 4,327,735, discloses a sleeve designed to protect the sterility of a catheter assembly, but does not hold a catheter balloon in wrapped condition. McFarlane, U.S. Pat. No. 4,573,981, discloses a sheath structure also designed to maintain catheter sterility, not to maintain a balloon in wrapped condition. Wolvek, et al., U.S. Pat. No. 4,444,186, discloses a wrapping guide which aids in spirally wrapping an intra-aortic balloon immediately before catheter use, but which does not hold the balloon tightly in a wrapped position.

This description of art is not intended to constitute an admission that any patent, publication, or other information referred to is "prior art" with respect to this invention unless specifically designated as such. In addition, this section should not be construed to mean that a search has been made or that no other pertinent information as defined in 37 C. F. R § 1.56 exists.

SUMMARY OF THE INVENTION

The present invention in one aspect is directed to elastomeric balloon protectors which exert continuous compressive force on the balloon to minimize wrapped balloon profile even when the protector has been removed. In another aspect, the invention is a balloon protector which can be used on a set of catheters with balloons of different sizes. In another aspect, the invention is a balloon protector which protects a balloon wrapped about a non-compressible inner lumen.

Specifically, in one aspect, the invention is a balloon protector for a balloon catheter comprising an elastomeric sleeve adapted to circumscribe the balloon of a balloon catheter, the sleeve having an inner diameter smaller than the outer diameter of the balloon so that it exerts continuous compressive force on the balloon. The balloon protector forms an interference fit with the wrapped balloon.

In the preferred embodiment, the balloon protector is in the form of a tube lined with a lubricious material to enhance removal of the protector from the balloon. The lubricious material may be a polymeric coating such as a silicone or a spray-on Teflon TM. The lubricious material may also be a Teflon TM tube, split lengthwise so that the compressive forces of the elastic tube are transmitted through the Teflon TM tube to the balloon within. The split is preferably tangential to the inner surface of the tube. The elastic sleeve is preferably formed of a silicone, and the durometer is preferably about 15 to 65, more preferably about 35 to about 50, and most preferably about 50.

In another aspect, the invention is a catheter system comprising an elongated shaft defining a lumen and having a distal and a proximal end; a balloon wrapped about the distal end of the shaft and in fluid communication with the lumen; and a balloon protector disposed about the wrapped balloon, the balloon protector comprising an elastic tube having an inner diameter smaller than the outer diameter of the wrapped balloon so that the protector exerts continuous compressive force on the balloon.

In the preferred embodiment, the catheter also includes an inner or guide wire lumen. The inner lumen is preferably non-compressible, or a stylet is included to prevent compression of the inner lumen. In addition, the balloon protector will preferably have the characteristics described earlier.

In another aspect, the invention is a method of compressing a balloon of a balloon catheter comprising the following steps:
providing a catheter having an elongated shaft and a balloon mounted thereon;
providing an elastomeric sleeve having an inner diameter smaller than the outer diameter; and
placing the balloon within the sleeve so that the sleeve compresses the balloon. The elastomeric sleeve provided preferably has the characteristics described earlier. A stylet may be inserted in the guidewire or inner lumen to prevent compression of a compressible guidewire lumen.

BRIEF DESCRIPTION OF THE DRAWINGS

FIGS. 2 through 4 are perspective views of the Teflon TM tube of the present invention, showing its preparation for insertion into the balloon protector.

FIG. 5 shows the balloon protector after manufacture.

FIG. 6 is a cross-section of the balloon protector of the present invention used with a catheter having a compressible guidewire lumen, showing the insertion of a stylet to prevent compression of the guidewire lumen.

DETAILED DESCRIPTION OF THE SPECIFIC EMBODIMENTS

Figure 1:
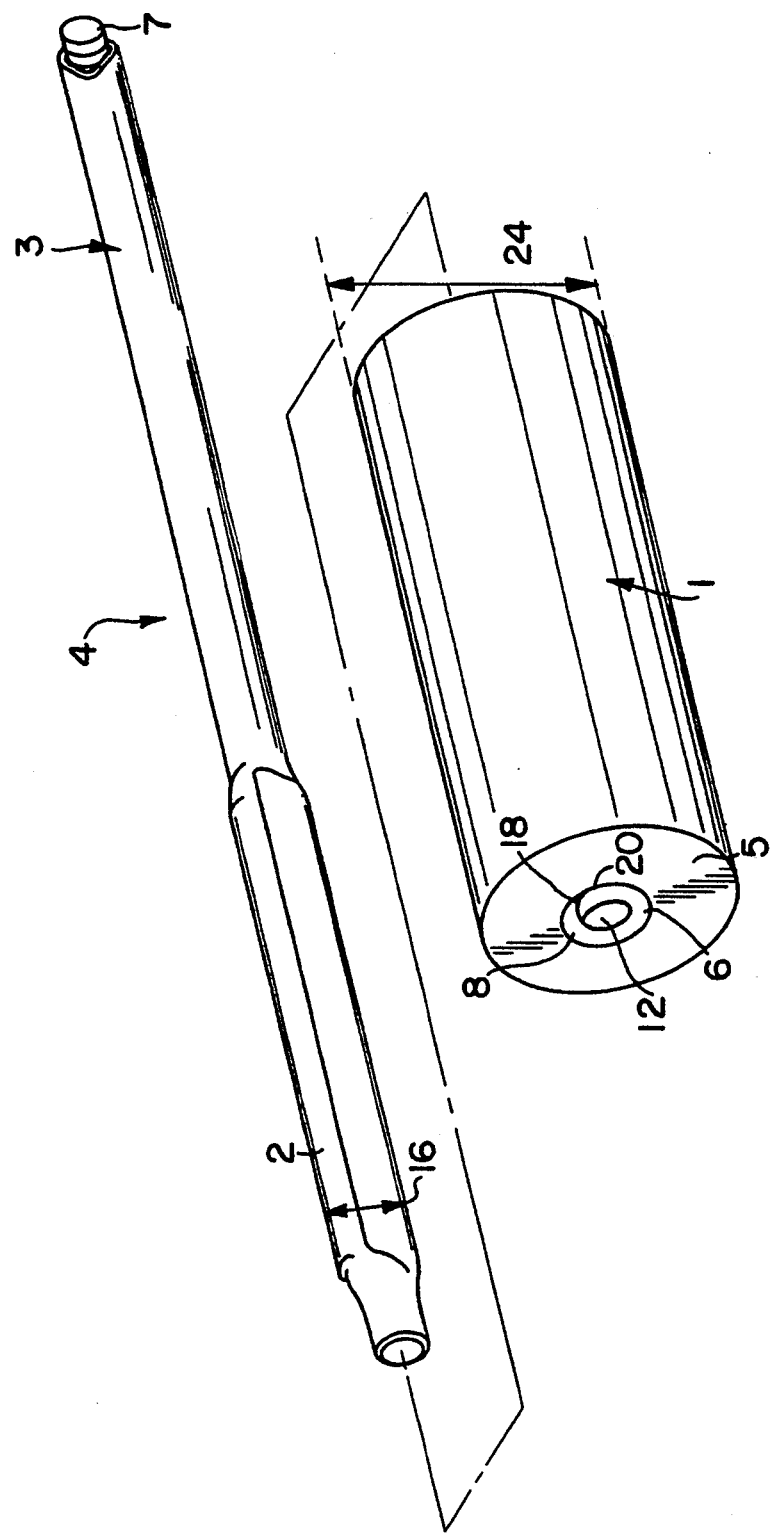
FIG. 1 is a perspective view of the balloon protector of the present invention, showing its placement over the balloon of a balloon catheter.

The present invention is an elastomeric compression member 1 comprised of tube or sleeve 5 shown in FIG. 5. In the preferred embodiment, it is used as a balloon protector for the balloon 2 of a balloon catheter 4 shown with the balloon and a portion of the shaft 3 in FIG. 1. In use, it is placed around the wrapped balloon of the catheter.

The balloon protector sleeve or tube 5 is formed of an elastomeric material such as silicone. The preferred material has a durometer (Shore A) of about 15 to 65, preferably about 35 to 50, most preferably about 50. Such a material will compress the balloon while it is in place. Further, it is resistant to heat shrinking at the temperatures at which the balloon, made of polyethylene, for example, is treated.

The preferred balloon protector 1 is formed with an interference fit with respect to the wrapped balloon 2. Specifically, the inner diameter 14 of the protector is smaller than the outer diameter 16 of the wrapped balloon. In the preferred embodiment, the inner diameter 14 of the tube is about 0.030 inch and the outer diameter 24 is about 0.100 inch.

The preferred balloon protector 1 has a lubricious inner surface which permits easy insertion of the balloon into the protector during manufacture and easy removal before the catheter is used. In one embodiment, the lubricious material is a coating, most preferably a silicone such as Dow MDX 4-4159. Other lubricious coatings, bonded or otherwise adhered to the surface, such as spray-on Teflon TM, are known to those of ordinary skill in the art.

In the embodiment shown, the lubricious inner surface is formed of a Teflon TM tube 6. Since Teflon TM is not sufficiently elastomeric, the tube is split lengthwise to define a longitudinal slit 8. The longitudinal slit allows the tube to be rolled into a smaller tube as shown in FIG. 4 so that it can be easily inserted into the outer elastomeric sleeve 5 during manufacture. Once slit, the two ends 18 and 20 of the Teflon TM tube tend to slide over each other while the balloon protector is in place, to accommodate balloons of varying diameters and to transmit the compressive forces of the outer elastic sleeve 5 through the liner 6 to the balloon. In the preferred embodiment, the inner diameter 22 of the Teflon TM tube (before it is inserted into the elastomeric sleeve) is about 0.065 inch and the outer diameter is about 0.075 inch. As a result, the effective inner diameter of the protector is smaller than that of the wrapped balloon (which has a diameter of about 0.029 to about 0.048 inches in the preferred catheter), and compressive forces are applied by the protector to the balloon.

The slit is preferably cut tangentially with respect to the inner surface 12 of the Teflon TM tube so that edges 18 and 20 of the Teflon TM tube 6 more easily slide over one another and damage to the balloon is minimized.

As shown in FIG. 1, the balloon protector 1 is part of a system including catheter 4. Catheter 4 includes an outer shaft 3 and an inner or guidewire lumen (or tube) 7. In the preferred catheter, the guidewire lumen is formed of a flat wire coil which is essentially non-compressible. Thus, it can be seen that in the preferred embodiment, the elastomeric compression unit forming the balloon protector holds the balloon in a tightly wrapped condition during heat shrinking, sterilization, and during storage of the catheter, the catheter itself being essentially non-compressible due to the spring coil inner lumen.

In the embodiment shown in FIG. 6, the catheter has a compressible inner lumen. A stylet 26 with endcap 28 is included to prevent collapse of the inner lumen. In this case, the stylet 26 is first inserted and balloon protector 1 then placed over the wrapped balloon. Finally, the endcap 28 is secured to the stylet as by crimping or gluing. Final processing of the catheter is then completed. When the balloon protector is ultimately removed, the stylet is pulled out simultaneously. In FIG. 6, a marker band 30 and inflation lumen 9 are shown.

The manufacture of the balloon protector is shown in FIGS. 2 through 5. The Teflon TM tube is first formed in a conventional manner, and then split longitudinally. It is then wrapped as shown in FIG. 4 and inserted into the sleeve 5 as shown in FIG. 5, where it retains a slightly wrapped configuration, with edges 18 and 20 lapped over each other.

From the foregoing detailed description of specific embodiments of the present invention, it should be apparent that an elastomeric compression unit particularly designed to protect the balloon of a balloon catheter has been described and a catheter system with a balloon protector has also been described. Although particular embodiments of the invention have been described herein in some detail, this has been done for the purposes of illustration only and is not intended to be limiting with respect to the scope of the invention. It has been contemplated by the inventors that various changes, alterations, or modifications may be made to the invention as described herein without departing from the spirit and scope of the invention as defined by the appended claims.

What is claimed is:

1. A balloon catheter system comprising:
   an elongated shaft having a distal end and a proximal end, and an inflation lumen running through the shaft;
   a balloon wrapped about the distal end of the shaft and the balloon in fluid communication with the inflation lumen; and
   a balloon protector disposed about the wrapped balloon, the balloon protector comprising:
   an elongated elastomeric sleeve with a longitudinal lumen running therethrough;
   an elongated tube within the lumen of the sleeve, the sleeve having an inner diameter smaller than the outer diameter of the uninflated wrapped balloon on a catheter when the sleeve is in a relaxed state, the tube having an inner diameter smaller than that of the uninflated wrapped balloon when the tube is in a relaxed state, and the tube being made of a lubricous material and having a longitudinal slit defining a first end and a second end, the ends overlapping each other.

2. A catheter system according to claim 1 wherein the tube is made of a different material than that of the sleeve.

3. A catheter system according to claim 1 wherein the tube is formed of Teflon TM.

4. A catheter system according to claim 1 wherein the sleeve is formed of a material having a durometer between about 15A and 65A.

5. A catheter system according to claim 1 wherein the sleeve is comprised of silicone.

6. A catheter system according to claim 1 wherein the slit is tangential to the inner surface of the tube.

7. A catheter system according to claim 1 wherein the shaft further comprises an inner lumen running through the inflation lumen, the inner lumen being sealed from the inflation lumen and extending to at least the distal end of the balloon.

8. A catheter system according to claim 7 wherein the inner lumen is substantially non-compressible.

9. A method of compressing a balloon of a balloon catheter comprising the steps of:
   providing a catheter having an elongated shaft and a balloon mounted thereon;
   providing an elastomeric sleeve;
   providing a tube with a longitudinal slit tangential to the inner surface of the tube;
   placing the tube in the sleeve;
   placing the balloon catheter in the tube; and
   removing the sleeve and tube prior to inserting the balloon catheter into the body.

10. A method of compressing the balloon of the balloon catheter according to claim 9 further comprising the step of providing the tube comprised of material having a durometer of about 15A to 65A.

* * * * *